US008685346B2

(12) United States Patent  
Logel et al.

(10) Patent No.: US 8,685,346 B2
(45) Date of Patent: Apr. 1, 2014

(54) VIAL (75) Inventors: Valere Logel, Levallois Perret (FR); Dominique Bois, Montreuil aux Lions (FR)

(73) Assignee: Clariant Production (France) S.A.S., Trosly Breuil (FR)

( * ) Notice: Subject to any disclaimer, the term of this patent is extended or adjusted under 35 U.S.C. 154(b) by 121 days.

(21) Appl. No.: 12/674,908

(22) PCT Filed: Aug. 27, 2008

(86) PCT No.: PCT/EP2008/061219
§ 371 (c)(1),
(2), (4) Date: May 23, 2011

(87) PCT Pub. No.: WO2009/030616
PCT Pub. Date: Mar. 12, 2009

(65) Prior Publication Data
US 2011/0210021 A1 Sep. 1, 2011

(30) Foreign Application Priority Data
Sep. 3, 2007 (EP) .................................. 07017242

(51) Int. Cl.
*A61B 10/00* (2006.01)
*B65D 43/16* (2006.01)
*B01L 9/00* (2006.01)

(52) U.S. Cl.
USPC ............ 422/561; 422/430; 206/204; 206/449

(58) Field of Classification Search
USPC .......... 206/204, 569, 540, 449; 422/558, 561, 422/430; 220/510, 512
See application file for complete search history.

(56) References Cited

U.S. PATENT DOCUMENTS 3,063,549 A * 11/1962 Weichselbaum .............. 206/456
5,270,011 A * 12/1993 Altherr ......................... 422/547
5,788,064 A *  8/1998 Sacherer et al. ............. 206/204
(Continued)

FOREIGN PATENT DOCUMENTS

EP        0454967 A2   11/1991
WO     WO9410558 A1    5/1994
(Continued)

OTHER PUBLICATIONS

European Search Report dated Feb. 25, 2008 with respect to the priority application, No. 07017242.4.
(Continued)

*Primary Examiner* — Mickey Yu
*Assistant Examiner* — Chun Cheung
(74) *Attorney, Agent, or Firm* — Scott R. Cox (57) ABSTRACT The present invention relates to a vial (10) for receiving goods (30) in a leak-proof arrangement, with a body (14) and a cap (12) connected via a hinge (16), the vial including a mold (26) for receiving lamellar goods (30), with the mold having a height which is less than the length of lamellar goods wherein a cavity (40) is formed between said mold receiving the stack of lamellar goods and the container body which cavity (40) receives desiccant material (44).

18 Claims, 6 Drawing Sheets

(56) References Cited

U.S. PATENT DOCUMENTS

| | | |
|---|---|---|
| 5,911,937 A | 6/1999 | Hekal |
| 6,497,845 B1 * | 12/2002 | Sacherer ............... 206/569 |
| 6,571,942 B2 * | 6/2003 | Riemenschneider et al. 206/204 |
| 6,872,358 B2 * | 3/2005 | Hagen et al. ............ 422/430 |
| 7,059,492 B2 * | 6/2006 | Giraud et al. ............ 220/834 |
| 7,670,562 B2 * | 3/2010 | Sacherer ............... 422/562 |
| 2005/0118071 A1 | 6/2005 | Sacherer |
| 2006/0013728 A1 * | 1/2006 | Moir ....................... 422/61 |
| 2006/0118570 A1 | 6/2006 | Fowler et al. |
| 2007/0080093 A1 | 4/2007 | Boozer et al. |
| 2007/0084749 A1 | 4/2007 | Demelo et al. |
| 2010/0140116 A1 * | 6/2010 | Stiene et al. ............ 206/204 |

FOREIGN PATENT DOCUMENTS

| | | |
|---|---|---|
| WO | WO9639343 A1 | 12/1996 |
| WO | WO2008092470 A1 | 8/2008 |
| WO | WO2008092639 A1 | 8/2008 |

OTHER PUBLICATIONS

Office Action dated Nov. 16, 2009 issued by the European Patent Office with respect to the priority application, No. 07017242.4.

Office Action dated Apr. 7, 2010 issued by the European Patent Office with respect to the priority application, No. 07017242.4.

* cited by examiner

VIAL

The present invention refers to a vial for receiving goods in a leak-poof arrangement, such as for medical applications, and preferably a vial for receiving lamellar goods like test strips etc.

The user will selectively take out one strip e.g. by turning the vial upside down. However, when turning such a vial upside down the user has to ensure that not more than one strip unintentionally drops from the vial.

To facilitate the handling, i.e. to prevent more than one test strip to drop from the vial, a narrow opening may be formed which is of such a shape that only one strip fits through it at the same time.

However, such vials tend to block this single opening, e.g. if a test strip breaks and there are Small remnant pieces of a test strip.

As an alternative arrangement it has been proposed to arrange the test strips in a stack or pile, and to withdraw the front strip manually in a controlled manner While the conventional test strip vials have a height which corresponds to the length of the test strips or is slightly greater than the length of the test strips, such vials have the stack or pile of test strips to protrude from the vial body.

The cover or cap of the vial must have a corresponding form. with a skirt extending downward in a sufficient manner to cover the upper end of the test strip stack and to safely close and seal the vial against environment moisture.

The user usually has to use both hands when taking out a test strip from the stack or pile. To do so, the user holds the vial body with one hand, and with the other hand isolates one of the strips from the remainder of stack in Order to take out. Then the cap usually is not held additionally but put somewhere e.g. an a desk. Thus, the cap can get lost, and with a lost cap the test strips are no longer protected again environment moisture.

Thus, this will deteriorate the test strip characteristics which even may fail when left in a humid environment.

Thus, it would be desireable to have a vial which is easier to handle and specifically adapted for the use of test strips.

Vials which shall be used for moisture-sensitive goods such as test strips will have to have some kind of desiccant in the inner space or receptacle of the vial. To receive such desiccants, it is well-known to form a desiccant compartment in the cap or stopper.

This arrangement however would considerably add to the overall height of the vial.

To avoid such problems, it has been proposed to arrange the test strips horizontally instead of vertically in a vial, and to withdraw them from a bottom opening, thus forming a test strip dispenser. However, it is difficult to ensure the safe sealing when such a form of a vial is used.

While the strips stand essentially upright or vertical when the vial is filled with the stack of strips, they tend to stand inclined client when the strips are being used up. Then the upper end of the cuter strip is subject to damages easily, especially when uncarefully closing the cap.

On the other hand, it is also known, e.g. from EP 454 967 A1 to provide the desiccant in the form of a molded insert arranged circumferentially in the vial body.

Therefore it is an object of the present invention to provide a vial according to claim 1 which is better suitable for receiving lamellar goods, especially if these goods are sensitive to humidity.

This object is settled by claim 1. Advantageous developments may be taken from the subclaims.

According to the invention, a cap for covering strips or other lamellar goods is provided with a hinge which is arranged between the cap and the vial body. This hinge allows to open and re-close the vial without the risk to lose the cap.

It may also be embodied as spring loaded hinge such that the cap stays wide open when opened. The stack may be guided and held in place by a mold which is formed such that its inner space meets the dimension of the stack of test strips. For the ease of withdrawal, the upper portion of the stack of strips is advantageously left entirely free such that each strips may be held at its side faces while the first and last strip may be gripped at its front and its rear surface respectively.

By leaving the stack of strips entirely free at its upper portion i.e. at about the upper 20% of its length the ease of withdrawal is improved while the mold allows a better guidance and presentation of the strips.

To avoid an inclined arrangement, the mold may be provided with small upright rims separating the stack of strips and keeping it upright.

The stack of strips is arranged close to the central or rear area of the vial body. Thus, the hinge guided cap does not touch the upper end of the test strips with its skirt even if the vial is nearly empty.

Closing and sealing is facilitated due to the easy construction of the closure cap which may be formed with a sealing lip allowing a snap fit closure. There is no need to turn the vial upside down to withdraw a single strip while on the other hand the arrangement of the desiccant at the lower portion of the vial improves the steadiness and tilt resistance of the vial.

The mold advantageously and automatically offers a hollow space which easily may be filled with desiccant. The amount of desiccant may be easily adapted to the desired shelf life of the vial, and also to the sort of goods which shall be received in the vial.

While the mold may be formed as an insert which preferable is snap-fit into the vial body, it is also possible to form the mold integrally with the outer vial body, with the desiccant being received in the hollow space between the mold and the vial body.

The hollow space between the mold and the body may be selected as desired and hollow space may be shaped and selected in a suitable manner to adapt the needs of desiccating and of keeping the strip in an upright position. The hollow space may be optimized up the maximum desired desiccant, and the filling volume thereof may be adapted to what is actually required, thus saving desiccant.

Also, the exchange rate of air, and, thus, of moisture through the membrane may be adjusted to the needs, by selecting a suitable membrane material and thickness.

While it is possible to use all of the hollow space, i.e. also the lateral parts surrounding the mold, the bottom portion thereof is preferred to receive most of the desiccant.

While the container body may have any form, it is preferred to use a cylindrical form allowing a circular seal surface between the body and the cap. On the other hand, the mold preferable has a cuboid inner space, presenting an accommodation for the stack of strips.

The mold insert may be provided with lateral support for the stack of test strips which improves the ability of the mold to hold the test strips in the desired position. Yet this support which protrudes from the mold surface does not conflict with the cap and the cap movement, and the strips are held centrally protruding from the upper rim of the vial body.

The distance between the stacked strips and the rim of the vial body both facilitates gripping of the test strips and prevents a conflict of with the vial cap.

Further features, characteristics and advantages may be taken from the following description of one embodiment of the present invention which is made with reference to the drawings.

Figure 2:
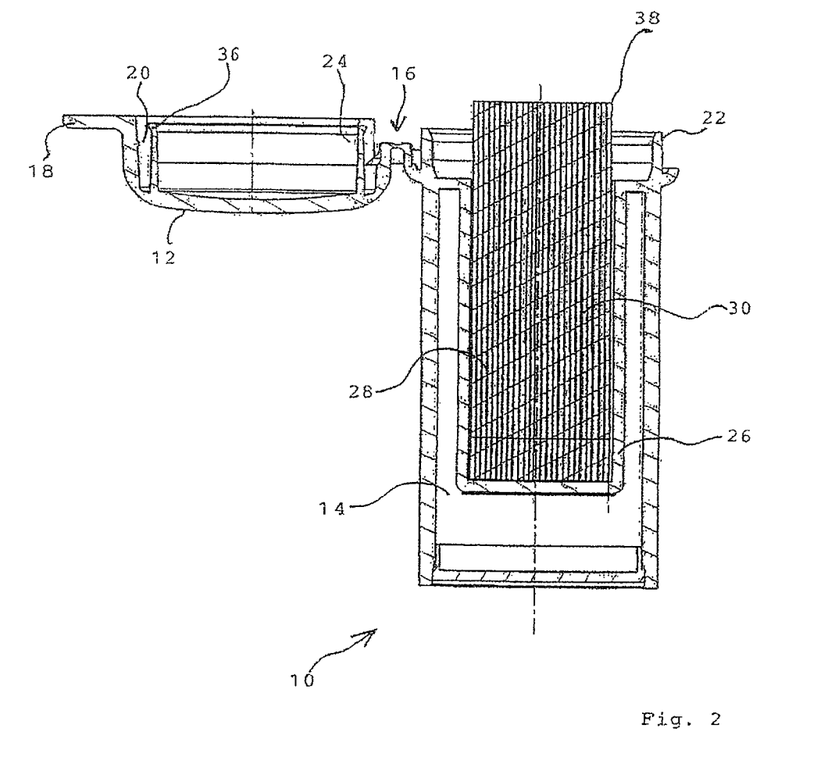
FIG. 2 shows the embodiment according to FIG. 1, in a different lateral sectional view.

A vial 10 comprises a vial body 14 and also a vial cap 12 which is shown in FIG. 2.

The vial 10 is provided with a mold 26 for receiving a stack 28 of lamellar goods which in the present embodiment are strips arranged in a piled form. The strips 30 stand upright in an inner space or receptacle 32 provided in the mold 26, and the strips 30 have a length of more then 90% of the Overall height of the vial 10. Thus, when opened, they protrude from the vial body 14 considerably, and the upper end portion 34 of the strips may easily be gripped. In the embodiment shown in FIG. 1, they have a convex shape 36 at the upper end portion 34. The size is adapted such that the strips are held in place 30 by abutting at the cap 12.

The vial 10 is further characterized in that the mold 26 is formed from a desiccant containing material, preferably a desiccant entrained polymer.

The stack 28 is built from strips which have about half of the width of the vial 10. They are arranged centrally such that there is no conflict when opening and closing the cap 12, between the inner edge 36 of the cap (see FIG. 2) the thumb tap 18, and the outer edge 38 of the strips (see also FIG. 2).

Moreover, it is preferred to arrange the stack 28 such that the strips with their width are essentially perpendicular to the axis of the hinge 16, i.e. other than shown in FIG. 2.

The receptacle 32 is essentially cuboid shaped to fit to the stack 28 of strips 30. It is provided in the mold 26 which leaves a cavity 40 to the outer wall 42 of body 14. This cavity 40 is preferably at least partially filled with desiccant. The cavity 40 may have several compartments or may at least have ribs for holding the desiccant 44 in place while air exchange is possible throughout the cavity 40.

To allow desiccating of the inner space or receptacle 32, the bottom 45 of mold 26 is provided with holes 50 which are covered by a meld or fleece 52. Any other suitable coverage, such as card board, possible as well.

It is also possible to avoid a mold or fleece and to select a suitably small diameter of the holes 50, e.g. from 0.1 mm to 0.5 mm.

Figure 1:
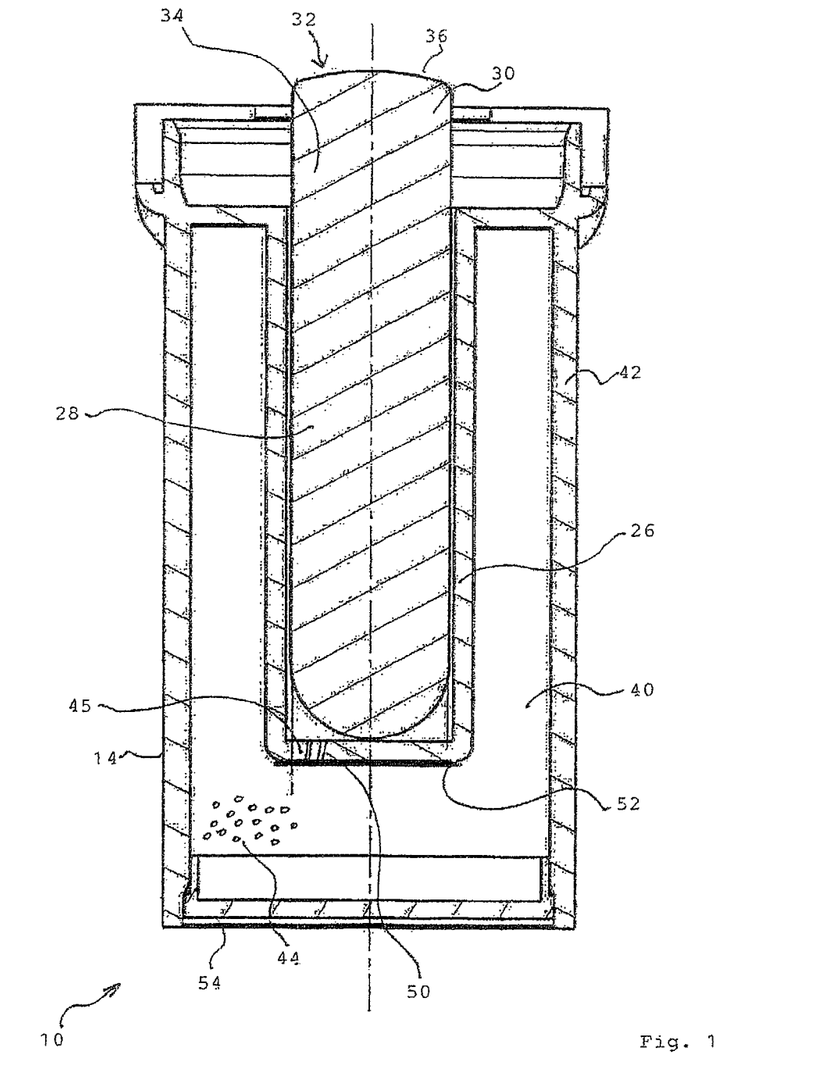
FIG. 1 shows a lateral sectional view of an embodiment of the vial according to the invention.

With the embodiment according to FIG. 1 and FIG. 2 the mold 26 is integrally formed with the container body 14. The lower end of the container body 14 is closed with a stopper or buckler 54 which allows to file cavity 40 with desiccant.

FIG. 2 shows the embodiment according to FIG. 1 in an other view. The cap 12 is connected with the vial body 14 via hinge 16. The hinge preferably is formed as a film hinge while alternatively a hinge construction with a plug and sleeve arrangement is possible. More preferably, the hinge is a spring-loaded hinge such that the cap 12 stays fully open when opened.

Opposite to the hinge 16, the cap 12 is provided with a thumb tab 18 and a sealing lip 20 provided at the cap 12 opposite to an upper rim 22 of the body 14 is arranged such that the vial is sealed against the entrance of the environment moisture when closed.

The vial body 14 extends over about 80% of the overall height of the vial 10. Thus, the cap 12 is provided with a relatively long skirt 24 extending over about 25% of the overall height of the vial 10.

The inner space 32 is filled with the stark 28 of strips 30. As long as the vial is filled with strips, all of them stand upright. However, if there are only few strips or a single strip 60, this strip will extend inclined. The upper end thereof will slightly protrude laterally but not to an extent that it comes into conflict with the skirt 24 of cap 12.

The stack 28 is in contact or nearly in contact with the inner side of mold 26 and the cap 12 when it is closed. The stack 28 thus is stabilized, and a disorder of the strips 30 is prevented.

Figure 3:
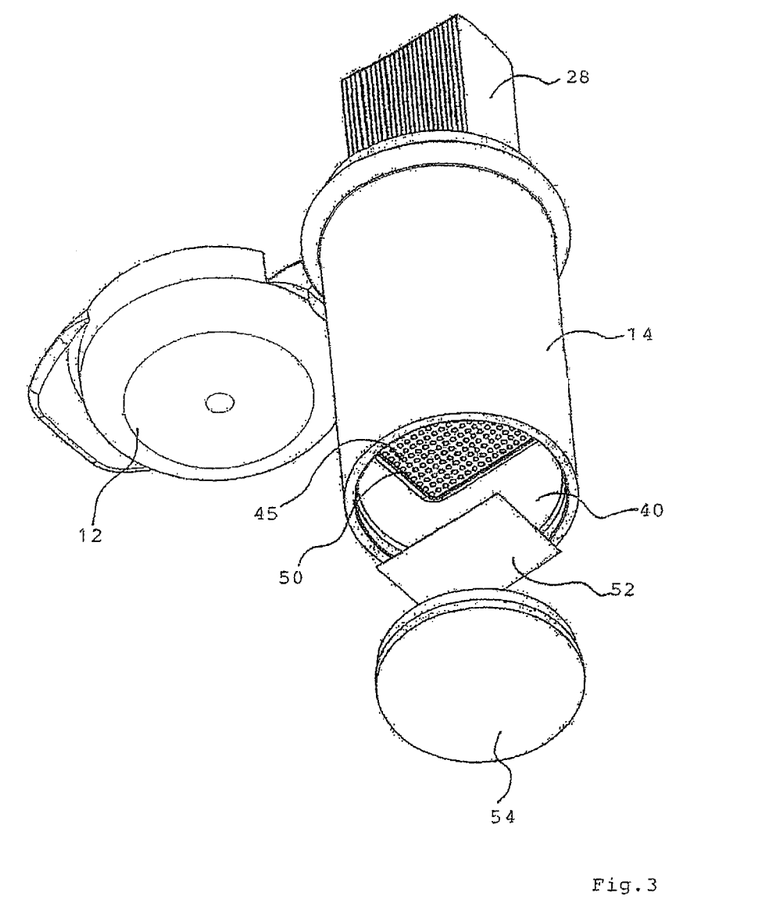
FIG. 3 shows the embodiment of FIG. 1 and 2, in a perspective exploded view.

FIG. 3 shows how the holes 50 may be arranged all over the bottom 45 of mold 26. All of the holes are covered by fleece 52, and the cavity 40 is closed by stopper 54.

In a preferred embodiment, the inner space 32 of the cap 12 includes a soft elastic element 19 for holding the lamellar goods, preferably a sponge or foam. (See FIG. 6.)

Figure 4:
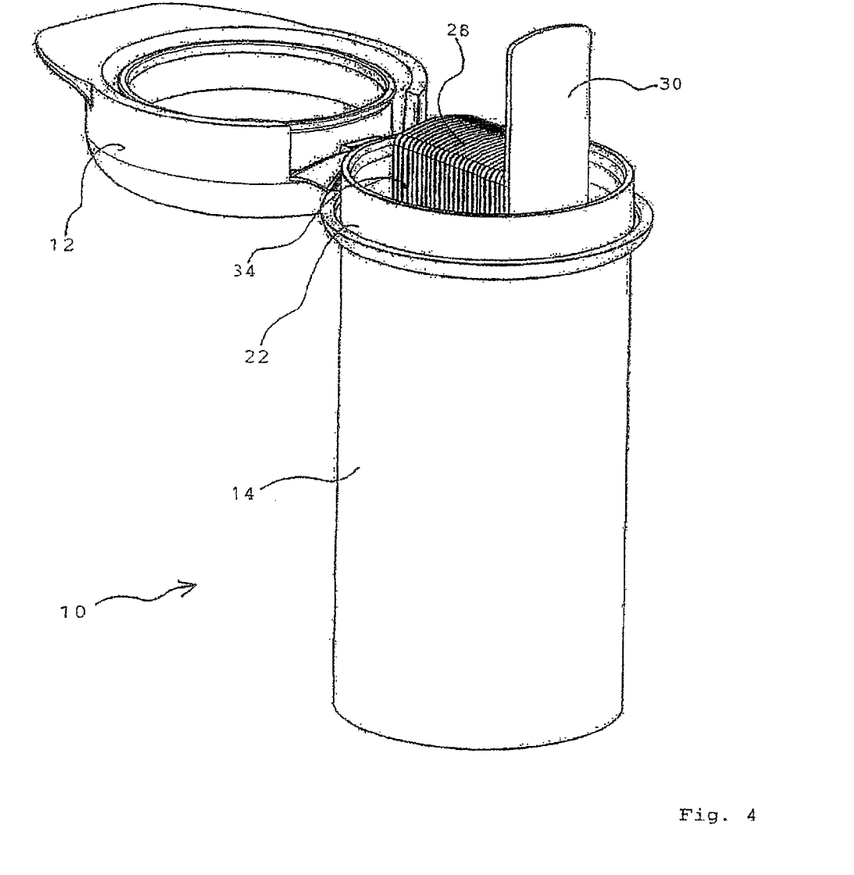
FIG. 4 shows a perspective view of the embodiment according to FIGS. 1 to 3.

FIG. 4 shows that due to the protrusion of the upper end 34 of the stack 28 over the upper rim 22 of the body 14; a single strip 30 may easily be gripped and extracted from the vial 10.

Figure 5:
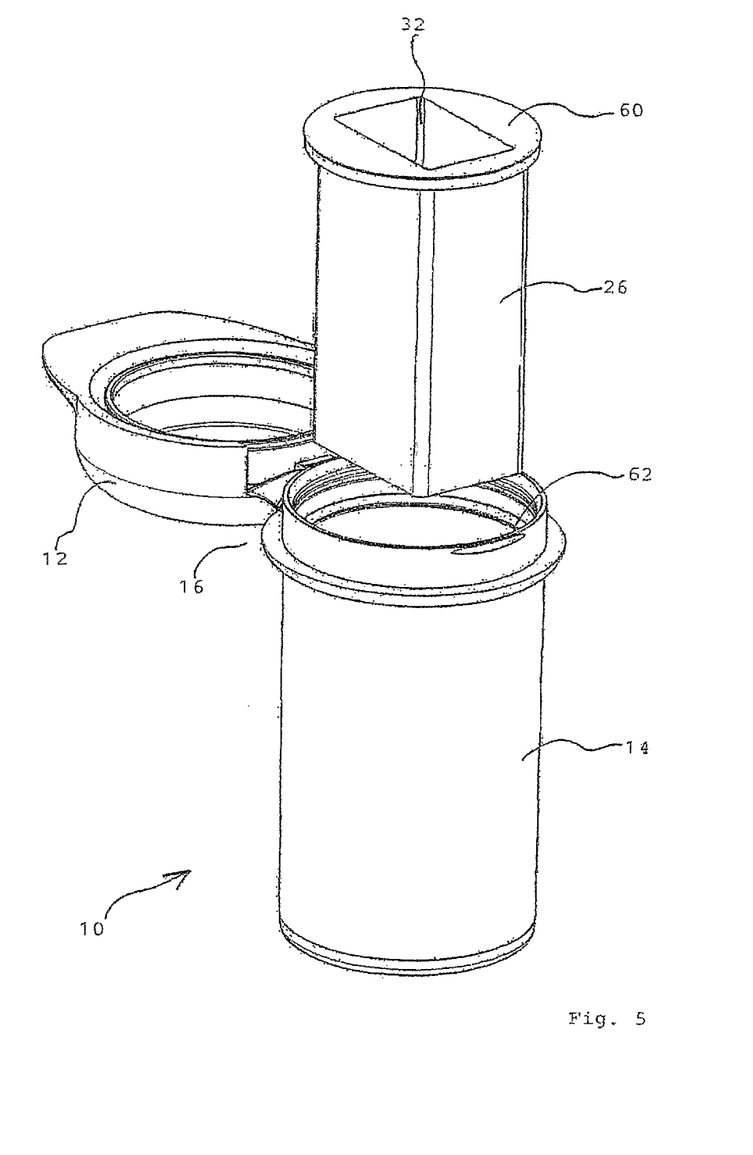
FIG. 5 shows a perspective view of a different embodiment of the invention.

FIG. 5 shows a different embodiment of the vial 10 according to the invention. With this embodiment, mold 26 is formed separately from the container body 14. The lid or cap 12 is connected to container body 14 via hinge 16, and in this arrangement, the mold 26 as also a cuboid inner space 32. The upper end of mold 26 is arranged with a circular flange 60 surrounding the receptacle 32 and adapted to fit an a respective shoulder 62 of the container body 14.

Figure 6:
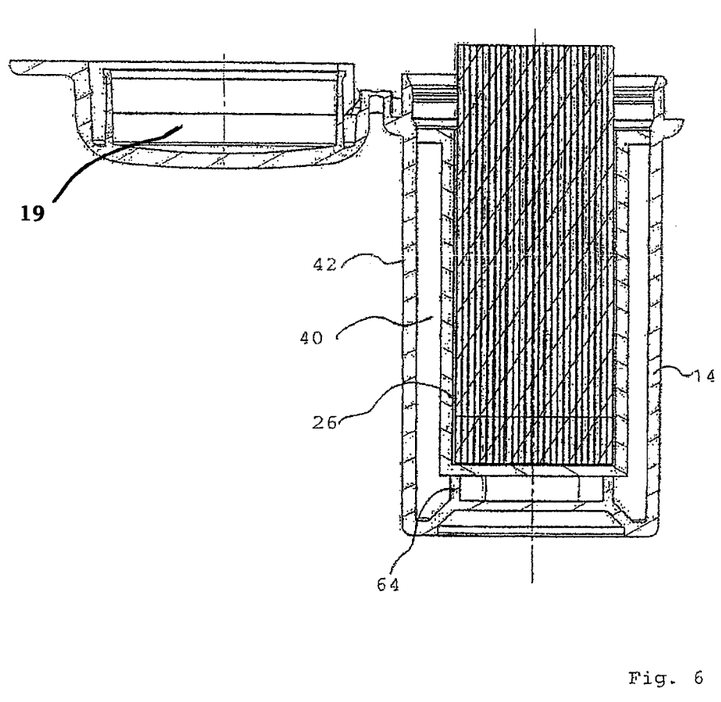
FIG. 6 shows a sectional view of the embodiment according FIG. 5.

FIG. 6 shows this arrangement in a sectional view. According to the embodiment shown in FIG. 6, the mold 26 is supported by upstanding ribs 64 extending from the bottom of container body 14. A hollow space or a cavity 40 is formed between wall 42 of the container body and the mold 26, as it is discussed above. This cavity 40 is filled with desiccant which may be inserted, either from the top side of body 14 before insertion of the mold 26, or from the bottom side. through a separate stopper which is not shown in FIG. 6.

The embodiment shown in FIG. 5 and FIG. 6 allows a better long-term density as there is only a single opening while the embodiment according to FIG. 1 to FIG. 4 allows an easier filling with desiccant.

While the upper form of the strips 30 is shown to be convex FIG. 1 and FIG. 3, it is also possible to have this form adapted to user's needs, e.g. to have the strips to end in a concave shape.

Also, it is possible to replace the circular and cylindrical shape of the container wall 42 by a form with flattened side walls, bringing the side walls closer to the mold at its, thus equalizing the thickness of the desiccant layer round the mold 26, and also facilitating user's grip.

The invention claimed is:

1. Vial for receiving goods in a leak-proof arrangement comprising a container body and a cap connected via a hinge, wherein the vial further comprises a mold and a stack of lamellar goods, which lamellar goods are within said mold, with the mold having a height which is less than the length of the lamellar goods, wherein a cavity is formed between said mold receiving the stack of lamellar goods and the container body which cavity contains desiccant, and wherein the width of the lamellar goods is less than the width of the vial, characterized in that
a lower end of the container body is closed with a stopper or buckler which permits the filling of the cavity with the desiccant,
the lamellar goods are arranged centrally within the mold of the vial such that interaction of the lamellar goods with the cap during opening and closing of the cap onto the container body is restricted;
wherein the cap is provided with a skirt which protrudes from a cap base of at least 15% up to 25% of the overall height of the vial.

2. Vial according to claim 1, characterized in that the vial has a free inner height which is from 5 to 20% larger than the height of the stack of the received lamellar goods comprising strips.

3. Vial according to claim 1, characterized in that the mold forms a receptacle for the lamellar goods and has a cuboid inner space.

4. Vial according to claim 1, characterized in that an inner space of the mold for receiving the lamellar goods has a width which is slightly wider than the width of the goods.

5. Vial according to claim 1, characterized in that the mold further comprises holes with a diameter which are smaller than the diameter of the lamellar goods and which holes are adjacent to the desiccant.

6. Vial according to claim 5, characterized in that the desiccant is separated from the holes by a disc produced from fleece or card board.

7. Vial according to claim 1, characterized in that that the cavity between a side wall of the container body and the mold is filled with desiccant.

8. Vial according to claim 1, characterized in that the mold is snapped into the container body and that the cavity receiving the desiccant is closed by a snap fit connection between the mold and the container body.

9. Vial according to claim 1, characterized in that the mold is formed as an insert which is secured to the container body.

10. Vial according to claim 1 characterized in that the mold is formed with the container body and forms a dual wall.

11. Vial according to claim 1, characterized in that the mold comprises an upper disc for at least one of sealing and closing against the container body.

12. Vial according to claim 1, characterized in that the container body is filled with the mold up to a height which is smaller than the overall height of the container body.

13. Vial according to claim 1, characterized in that the container body has an upper rim surrounding the mold, and said upper rim is upstanding from the mold.

14. Vial according to claim 1, characterized in that an inner space of the cap is at least partially filled with an upper end of the lamellar goods when the cap is closed on the body.

15. Vial according to claim 14, characterized in that the inner space of the cap comprises a soft elastic element for holding the upper end of the lamellar goods, comprising a sponge or foam.

16. Vial according to claim 1, characterized in that the hinge between the cap and the container body comprises a spring hinge holding the cap in the full open position when the cap is opened.

17. Vial according to claim 1, characterized in that the mold is formed from a desiccant containing material.

18. Vial according to claim 1, characterized in that the vial has a non-circular cross-section comprising flattened side walls.

* * * * *